(12) United States Patent
Braig et al.

(10) Patent No.: US 8,242,191 B2
(45) Date of Patent: Aug. 14, 2012

(54) PROCESS FOR PRODUCING WATER-ABSORBING POLYMER PARTICLES

(75) Inventors: Volker Braig, Weinheim-Lützelsachsen (DE); Thomas Daniel, Waldsee (DE); Axel Jentzsch, Ludwigshafen (DE); Andreas Brockmeyer, Alsbach-Hähnlein (DE)

(73) Assignee: BASF SE, Ludwigshafen (DE)

( * ) Notice: Subject to any disclaimer, the term of this patent is extended or adjusted under 35 U.S.C. 154(b) by 219 days.

(21) Appl. No.: 12/612,302

(22) Filed: Nov. 4, 2009

(65) Prior Publication Data
US 2010/0119830 A1 May 13, 2010

Related U.S. Application Data

(60) Provisional application No. 61/112,454, filed on Nov. 7, 2008.

(51) Int. Cl.
*C08K 5/13* (2006.01)
*B01J 20/26* (2006.01)

(52) U.S. Cl. ....... 524/72; 524/435; 524/556; 526/317.1; 502/402; 428/407

(58) Field of Classification Search .......... 502/402; 524/556, 72, 435; 526/317.1; 428/407
See application file for complete search history.

(56) References Cited

U.S. PATENT DOCUMENTS

| | | | |
|---|---|---|---|
| 6,359,049 B1 * | 3/2002 | Carrico et al. | 524/414 |
| 2003/0004479 A1 * | 1/2003 | Ueda et al. | 604/359 |
| 2004/0048955 A1 * | 3/2004 | Wada et al. | 524/9 |
| 2007/0066167 A1 * | 3/2007 | Wada et al. | 442/101 |
| 2007/0141338 A1 * | 6/2007 | Ishizaki et al. | 428/402 |
| 2007/0225160 A1 * | 9/2007 | Kitano et al. | 502/402 |
| 2008/0161512 A1 * | 7/2008 | Kawano et al. | 526/123.1 |

FOREIGN PATENT DOCUMENTS

| | | |
|---|---|---|
| EP | 257951 A2 * | 3/1988 |
| EP | 150 562 A1 | 3/2005 |
| WO | WO 2006/109842 A1 | 10/2006 |
| WO | WO 2009/040106 A2 | 4/2009 |

OTHER PUBLICATIONS

"Solution Polymerization: Unit Operations and Their Effect on Product Quality," from *Modern Superabsorbent Polymer Technology*. Bucholz et al., Eds., John Wiley & Sons, Inc., 71-103, (1998).

* cited by examiner

*Primary Examiner* — David W Wu
*Assistant Examiner* — Vu A Nguyen
(74) *Attorney, Agent, or Firm* — Marshall, Gerstein & Borun LLP

(57) ABSTRACT

A process for producing odor-inhibiting water-absorbing polymer particles based on ethylenically unsaturated monomers bearing acid groups, wherein the acid groups have been neutralized to an extent of from 40 to 70 mol % and the polymer particles are coated with a condensed tannin and/or a hydrolyzable tannin.

16 Claims, No Drawings

PROCESS FOR PRODUCING WATER-ABSORBING POLYMER PARTICLES

CROSS-REFERENCE TO RELATED APPLICATIONS

This application claims the benefit of U.S. Provisional Patent Application No. 61/112,454, filed Nov. 7, 2008, incorporated herein by reference in its entirety.

The invention relates to a process for producing odor-inhibiting water-absorbing polymer particles based on ethylenically unsaturated monomers bearing acid groups, wherein the acid groups have been neutralized to an extent of from 40 to 70 mol % and the polymer particles are coated with a condensed tannin and/or a hydrolyzable tannin.

The production of water-absorbing polymer particles is described in the monograph "Modern Superabsorbent Polymer Technology", F. L. Buchholz and A. T. Graham, Wiley-VCH, 1998, pages 71 to 103.

Water-absorbing polymers are used to produce diapers, tampons, sanitary napkins and other hygiene articles, but also as water-retaining agents in market gardening.

EP 1 510 562 A1 describes the production of odor-inhibiting water-absorbing polymer particles, where the polymer particles are coated with plant extracts, which may comprise tannin or tannic acid among other substances.

WO 2006/109842 A1 describes a process for producing water-absorbing polymer particles, wherein a monomer solution with a defined content of hydroquinone monomethyl ether and iron and a small amount of protoanemonin and furfural is polymerized.

It was an object of the present invention to provide an improved process for producing odor-inhibiting water-absorbing polymer particles.

The object is achieved by a process for producing water-absorbing polymer particles, comprising
i) the neutralization of at least one ethylenically unsaturated monomer bearing acid groups with a base up to a degree of neutralization of from 40 to 70 mol %, the base comprising less than 0.0005% by weight of iron ions and the lines used to convey the base being made of stainless steel or a polymeric material,
ii) polymerization of the neutralized monomer in the presence of at least one crosslinker and of at least one initiator, the initiator being essentially free of iron ions,
iii) drying of the resulting polymer gel,
iv) comminution of the dried polymer gel to polymer particles,
v) classification of the resulting polymer particles and
vi) optional surface postcrosslinking of the classified polymer particles,
the polymer particles being coated with from 0.01 to 1% by weight of at least one condensed and/or a hydrolyzable tannin.

The degree of neutralization is preferably from 45 to 65 mol %, more preferably from 48 to 62 mol %, most preferably from 50 to 60 mol %.

The base comprises preferably less than 0.0001% by weight, more preferably less than 0.00002% by weight, and most preferably less than 0.00001% by weight, of iron ions.

Suitable stainless steels are austenitic steels with, for example, at least 0.08% by weight of carbon. The austenitic steels advantageously comprise, as well as iron, carbon, chromium, nickel and optionally molybdenum, also further alloy constituents, preferably niobium or titanium.

The preferred stainless steels are stainless steels with materials number 1.45xx according to DIN EN 10020, where xx may be a natural number from 0 to 99. Particularly preferred materials are the steels with materials numbers 1.4541 and 1.4571, especially steel with materials number 1.4541.

Suitable polymeric materials are polyethylene, polypropylene, polyester, polyamide, polytetrafluoroethylene, polyvinyl chloride, epoxy resins and silicone resins. Very particular preference is given to polypropylene.

The initiator systems used are essentially free of iron ions, the initiator systems used comprising preferably less than 0.1% by weight, more preferably less than 0.01% by weight, and most preferably less than 0.001% by weight, or iron ions, based in each case on the total amount of the initiator system.

Suitable condensed tannins are polymeric flavan-3-ols based on epicatechin and catechin or polymeric flavan-3,4-diols based on leucopelargonidine.

Suitable hydrolyzable tannins are esters of saccharides, such as glucose, with gallic acids, such as gallic acid, galloylgallic acid and digalloylgallic acid.

The polymer particles are preferably coated with from 0.02 to 0.5% by weight, more preferably from 0.05 to 0.3% by weight, and most preferably from 0.1 to 0.2% by weight, of condensed and/or hydrolyzable tannins.

The coating of the polymer particles is preferably performed by means of mixers with mobile mixing tools. The mixers usable for surface postcrosslinking can also be used for the inventive coating.

It is possible to coat the polymer particles obtained after the classification v) or those obtained after the optional surface postcrosslinking vi) with a complexing agent. Moreover, it is possible to perform the coating simultaneously with the surface postcrosslinking.

Preferably, the polymer particles are coated by spraying the chelating agents onto the polymer particles as a solution in a suitable solvent, preferably water.

In a preferred embodiment of the present invention, the water-absorbing polymer particles are coated with a reducing agent and/or a zinc salt.

Suitable reducing agents are for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to using salts of hypophosphorous acid for example sodium hypophosphite, and salts of sulfinic acids, for example the disodium salt of 2-hydroxy-2-sulfinatoacetic acid. However, the reducing agent used is preferably a mixture of the sodium salt of 2-hydroxy-2-sulfinatoacetic acid, the disodium salt of 2-hydroxy-2-sulfonatoacetic acid and sodium bisulfite. Such mixtures are available as Brüggolite® FF6 and Brüggolite® FF7 (Brüggemann Chemicals; Heilbronn; Germany).

The amount of reducing agent used is preferably from 0.01 to 5% by weight, more preferably from 0.05 to 2% by weight, and most preferably from 0.1 to 1% by weight, in each case based on the water-absorbing polymer.

Suitable zinc salts are, for example, zinc hydroxide, zinc sulfate, zinc chloride, zinc citrate, zinc acetate and zinc lactate. Preference is given to using zinc salts of fatty acids, for example of ricinoleic acid.

The amount of zinc salt used is preferably from 0.01 to 5% by weight, more preferably from 0.05 to 3% by weight, and most preferably from 0.1 to 1% by weight, based in each case on the water-absorbing polymer.

The reducing agents and/or zinc salts are typically used in the form of a solution in a suitable solvent, preferably water.

The present invention is based on the finding that the combination of slightly acidic water-absorbing polymer particles with condensed and/or hydrolyzable tannins lead to significantly improved odor inhibition, but undesired discoloration occurs at the same time. The discoloration is triggered by traces of iron ions. Strict control of the amount of iron ions makes it possible to provide water-absorbing polymer particles which firstly have good odor inhibition and secondly have a low discoloration tendency.

An example of a possible source for iron ions is sodium hydroxide solution, which is frequently used as a base. To perform the process according to the invention it should be ensured that the sodium hydroxide solution used has a minimum proportion of iron ions.

In addition, the pipelines in which the base is sent to the neutralization are critical. For instance, sodium hydroxide solution is not considered to be corrosive with respect to unalloyed steels and is even used for passivation. However, sodium hydroxide solution leaches small traces of iron ions from unalloyed steels. The base therefore has to be conveyed into the neutralization by means of a pipeline made of stainless steel or a polymeric material. Owing to the associated lower input of iron ions, it is advantageous also to use stainless steel or a polymeric material as the material for the remaining plant parts of the preparation process which are in contact with the product.

Moreover, it should be ensured that an initiator system is used, in which substantially no iron ions are used as a catalyst.

Additional coating of the polymer particles with reducing agents and/or zinc salts allows the discoloration tendency to be further influenced favorably.

The production of the water-absorbing polymer particles is described in detail hereinafter.

The water-absorbing polymer particles are produced, for example, by polymerizing a monomer solution or suspension comprising
a) at least one ethylenically unsaturated monomer bearing acid groups wherein the acid groups have been neutralized to an extent of from 40 to 70 mol %,
b) at least one crosslinker,
c) at least one initiator,
d) optionally one or more ethylenically unsaturated monomers copolymerizable with the monomers mentioned under a) and
e) optionally one or more water-soluble polymers,
and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone nnonoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/ sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a be/tis described, for example, in DE 38 25 366 A1 and U.S. Pat. No. 6,241,928. Polymerization in a belt reactor forms a polymer gel, which has to be comminuted in a further process step, for example in an extruder or kneader.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 45 to 65 mol %, more preferably from 48 to 62 mol %, most preferably from 50 to 60 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, potassium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably from 0.5 to 15% by weight, more preferably from 1 to 10% by weight, most preferably from 2 to 8% by weight, the residual moisture content being determined by the EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of the EDANA (European Disposables and Nonwovens Association) recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until in an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably from 0.001 to 2% by weight, more preferably from 0.02 to 1% by weight and most preferably from 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened.

The subsequent moistening is carried out preferably at from 30 to 80° C., more preferably at from 35 to 70° C. and most preferably at from 40 to 60° C. At excessively low temperatures, the water-absorbing polymer particles tend to form lumps, and, at higher temperatures, water already evaporates noticeably. The amount of water used for subsequent moistening is preferably from 1 to 10% by weight, more preferably from 2 to 8% by weight and most preferably from 3 to 5% by weight. The subsequent moistening increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired packing tendency of the polymer particles are, for example, fumed silica, such as Aerosil® 200, and surfactants, such as Span® 20.

The present invention further provides the water-absorbing polymer particles produced by the process according to the invention.

The water-absorbing polymer particles produced by the process according to the invention have a low content of iron ions. The content of iron ions is less than 0.001% by weight, preferably less than 0.0005% by weight, more preferably less than 0.0001% by weight and most preferably less than 0.00002% by weight.

Also important is a sufficient excess of condensed and/or hydrolyzable tannin compared to the iron ions. The weight ratio of iron ions to condensed and/or hydrolyzable tannin is less than 0.02, preferably less than 0.01, more preferably less than 0.005 and most preferably less than 0.001.

The water-absorbing polymer particles produced by the process according to the invention have a moisture content of preferably from 1 to 10% by weight, more preferably from 2 to 8% by weight, most preferably from 3 to 5% by weight, the water content being determined by the EDANA (European Disposables and Nonwovens Association) recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA (European Disposables and Nonwovens Association) recommended test method No. WSP 241.2-05 "Centrifuge Retention Capacity".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to the EDANA (European Disposables and Nonwovens Association) recommended test method No. WSP 242.2-05 "Absorption under Pressure", except that a pressure of 49.2 g/cm$^2$ is established instead of a pressure of 21.0 g/cm$^2$.

The present invention also provides hygiene articles comprising water-absorbing polymer particles produced by the process according to the invention, especially hygiene articles for feminine hygiene, hygiene articles for mild and severe incontinence, or small animal litter.

EXAMPLES

The following solutions were prepared:
1. 16.67 g of gallotannin (tannic acid; CAS no. [1401-55-4]; ABCR GmbH & Co. KG; Germany) were weighed into a wide-neck glass vessel and made up to 100.02 g with dist. water. For complete dissolution, the vessel was heated gently in a water bath (approx. 40° C.).
2. 1.67 g of iron sulfate hydrate (86.0-89.0% FeSO$_4$; CAS no. [13463-43-9]; Riedel-de Häen) were weighed into a wide-neck glass vessel and made up to 100.10 g with dist. water.
3. 16.72 g of gallotannin (tannic acid; CAS no. [1401-55-4]; ABCR GmbH & Co. KG; Germany) and 1.70 g of iron sulfate hydrate (86.0-89.0% FeSO$_4$; CAS no. [13463-43-9]; Riedel-de Häen) were weighed into a wide-neck glass vessel and made up to 100.13 g with dist. water. For complete dissolution, the vessel was heated gently in a water bath (approx. 40° C.).

20.0 g of water-absorbing polymer particles (HySorb® B7065; BASF SE; Germany) were introduced into a modified coffee grinder (Blender 8012 Model 34BL99; Waring Laboratory; US) with an attachment made of stainless steel (internal diameter 8 cm, internal height 4 cm, tool diameter 7 cm, addition point in the lid 1.3 cm from the edge, baffles in the lid). The modified coffee grinder was operated at level 3. A syringe with a cannula was used to slowly add in each case 0.60 g of the particular solution. After the end of the addition, the water-absorbing polymer particles were transferred to a glass dish and dried at 50° C. in a drying cabinet for 30 minutes. For better homogenization, the water-absorbing polymer particles were triturated with a pestle in a porcelain mortar (internal diameter 8.5 cm) for 10 minutes.

The color of the samples was analyzed with a spectrophotometer (LabScan XE; Hunter Associates Laboratory, Inc.; US). The water-absorbing polymer particles (SAPs) were introduced in the lid of a polystyrene Petri dish (internal diameter 3.9 cm) and analyzed with the following settings:
Pot size: 1.2 inches
Viewing Area: 1 inch
Illuminant: C
Observer: 2°

| SAP with | L | a | b |
| --- | --- | --- | --- |
| Solution 1 | 89.02 | −0.4 | 6.5 |
| Solution 2 | 88.88 | −0.43 | 3.51 |
| Solution 3 | 64.49 | 3.92 | 1.29 |

It can be seen that the water-absorbing polymer particles treated with solution 3 have a smaller L value and are thus less white.

The invention claimed is:

1. Water-absorbing polymer particles, obtained by polymerizing an aqueous monomer solution or suspension, comprising
    a) at least one ethylenically unsaturated monomer bearing acid groups wherein the acid groups have been neutralized to an extent of from 40 to 70 mol %,
    b) at least one crosslinker and
    c) at least one initiator,
the polymer particles comprising less than 0.001% by weight of iron ions and being coated with from 0.01 to 1% by weight of at least one condensed and/or hydrolyzable tannin, where the weight ratio of iron ions to condensed and/or hydrolyzable tannin is less than 0.02.

2. Polymer particles according to claim 1, which have been coated with polyvalent cations.

3. Polymer particles according to claim 1, which have been surface post-crosslinked with a compound which can form covalent bonds with at least two carboxylate groups of the water-absorbing polymer particles.

4. Polymer particles according to claim 1, wherein at least 95% of which have a particle size of from 150 to 600 pm.

5. Polymer particles according to claim 1, which have a moisture content of from 1 through 10% by weight.

6. Polymer particles according to claim 1, which have been coated with at least one reducing agent.

7. Polymer particles according to claim 1, which have been coated with at least one zinc salt.

8. Polymer particles according to claim 1, which have a centrifuge retention capacity of from 15 to 60 g/g, as determined by EDANA test method No. WSP 241.2-05.

9. Polymer particles according to claim 1, which have an absorption under a pressure of 49.2 $g/cm^2$ of from 15 to 35 g/g, as determined by EDANA test method No. WSP 242.2-05.

10. A hygiene article comprising polymer particles according to claim 1.

11. Polymer particles according to claim 1 comprising less than 0.0005% by weight of iron ions.

12. Polymer particles according to claim 1 comprising less than 0.0001% by weight of iron ions.

13. Polymer particles according to claim 1 comprising less than 0.00002% by weight of iron ions.

14. Polymer particles according to claim 1 where the weight ratio of iron ions to condensed and/or hydrolysable tannins is less than 0.01.

15. Polymer particles according to claim 1 where the weight ratio of iron ions to condensed and/or hydrolysable tannins is less than 0.005.

16. Polymer particles according to claim 1 where the weight ratio of iron ions to condensed and/or hydrolysable tannins is less than 0.001.

* * * * *